(12) United States Patent
Allen et al.

(10) Patent No.: US 7,557,264 B2
(45) Date of Patent: Jul. 7, 2009

(54) *GOSSYPIUM HIRSUTUM* TISSUE-SPECIFIC PROMOTERS AND THEIR USE

(75) Inventors: Randy D. Allen, Lubbock, TX (US); Ping Song, Carmel, IN (US)

(73) Assignee: Texas Tech University, Lubbock, TX (US)

( * ) Notice: Subject to any disclaimer, the term of this patent is extended or adjusted under 35 U.S.C. 154(b) by 159 days.

(21) Appl. No.: 10/343,810

(22) PCT Filed: Aug. 7, 2001

(86) PCT No.: PCT/US01/24846

§ 371 (c)(1),
(2), (4) Date: Oct. 24, 2003

(87) PCT Pub. No.: WO02/12450

PCT Pub. Date: Feb. 14, 2002

(65) Prior Publication Data

US 2004/0088760 A1 May 6, 2004

Related U.S. Application Data

(60) Provisional application No. 60/223,496, filed on Aug. 7, 2000.

(51) Int. Cl.
*C12N 15/11* (2006.01)
*C12N 15/63* (2006.01)
*C12N 15/67* (2006.01)
*C12N 15/82* (2006.01)
*A01H 5/00* (2006.01)

(52) U.S. Cl. .................. 800/287; 800/281; 800/295; 800/314; 435/320.1; 435/427; 435/468; 536/23.1; 536/24.1

(58) Field of Classification Search ........... None
See application file for complete search history.

(56) References Cited

U.S. PATENT DOCUMENTS

| 5,495,070 A | * | 2/1996 | John ................. 800/287 |
| 5,521,078 A | | 5/1996 | John |
| 5,602,321 A | | 2/1997 | John |
| 5,608,148 A | | 3/1997 | John |
| 5,792,933 A | | 8/1998 | Ma |
| 5,846,797 A | * | 12/1998 | Strickland ............ 800/294 |
| 5,850,016 A | * | 12/1998 | Jung et al. ............ 800/287 |
| 5,850,026 A | * | 12/1998 | DeBonte et al. ......... 800/281 |
| 5,869,720 A | | 2/1999 | John |
| 5,932,713 A | | 8/1999 | Kasukabe et al. |
| 6,040,504 A | * | 3/2000 | Rice et al. ............ 800/314 |

FOREIGN PATENT DOCUMENTS

| JP | 10201474 | 8/1998 |
| JP | 10215870 | 8/1998 |
| JP | 10215871 | 8/1998 |

OTHER PUBLICATIONS

Dure III, L. 1993 G. hirsutum storage protein (late embryogenesis abundant) gene, complete cds, clone D34. Direct submission GenBank accession M19389.*
Benfey et al, 1990, Science 250:959-966, p. 960.*
Kim et al, 1994, Plant Molecular Biology 24:105-117, p. 108.*
McDonald et al, EMBO Journal 9:1717-1726, p. 1718 and 1719.*
Dolferus et al, 1994, Plant Physiology 105:1075-1087, e.g., pp. 1080-1082.*
Dure III, L. 1993 G. hirsutum stoage protein (late embryogenesis abundant) gene, complete cds, clone D34. Direct submission GenBank accession M19389.*
Baker et al 1988 Plant Molecular Biology 11:277-291.*
Genbank Accession No. M19389 (Apr. 27, 1993).
Genbank Accession No. X54091 (Jan. 25, 1994).
Hudspeth et al., "Characterization and Expression of Metallothionein-Like Gene in Cotton," *Plant Mol. Biol.* 31:701-705 (1996).
John & Crow, "Gene Expression in Cotton (*Gossypium hirsutum* L.) Fiber: Cloning of the mRNAs," *Proc. Natl. Acad. Sci. USA* 89:5769-5773 (1992).
John, "Structural Characterization of Genes Corresponding to Cotton Fiber mRNA, E6: Reduced E6 Protein in Transgenic Plants by Antisense Gene," *Plant Mol. Biol.* 30:297-306 (1996).
Rinehart et al., "Tissue-Specific and Developmental Regulation of Cotton Gene *FbL2A*," *Plant Physiol.* 112:1331-1341 (1996).

(Continued)

*Primary Examiner*—Russell Kallis
*Assistant Examiner*—Brent Page
(74) *Attorney, Agent, or Firm*—Kammer Browning PLLC

(57) ABSTRACT

The present invention relates to an isolated DNA molecule selected from the group: a promoter-effective DNA molecule of *Gossypium* which is operable in embryonic seed tissues and a promoter-effective DNA molecule of *Gossypium* which is operable in chlorophyllous tissues. Use of the promoter-effective DNA molecules in chimeric genes, and preparation of expression systems, host cells, transgenic plants, and transgenic plant seeds containing such chimeric gene is also disclosed. Methods of expressing a heterologous mRNA molecule or protein or polypeptide in chlorophyllous tissue of plants or embryonic seed tissues are also disclosed.

35 Claims, 4 Drawing Sheets

OTHER PUBLICATIONS

Sagliocco et al., "Sequence of an *rbcS* Gene from Cotton," *Plant Molecular Biology* 17:1275-1276 (1991).

Song et al., "Expression of Two Tissue-Specific Promoters in Transgenic Cotton Plants," *J. Cotton Sci.* 4:217-223 (2000).

Baker et al., "Sequence and Characterization of 6 Lea Proteins and Their Genes from Cotton," Plant Molecular Biology 11:277-291 (1988).

* cited by examiner

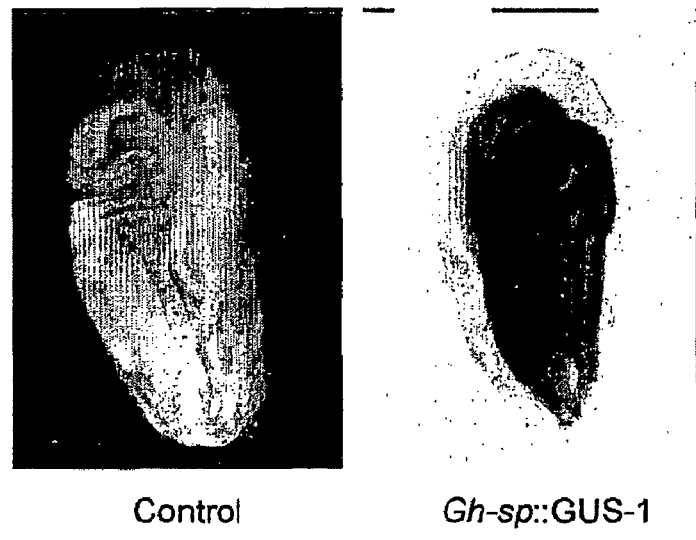
Control      Gh-sp::GUS-1
Figure 3A      Figure 3B
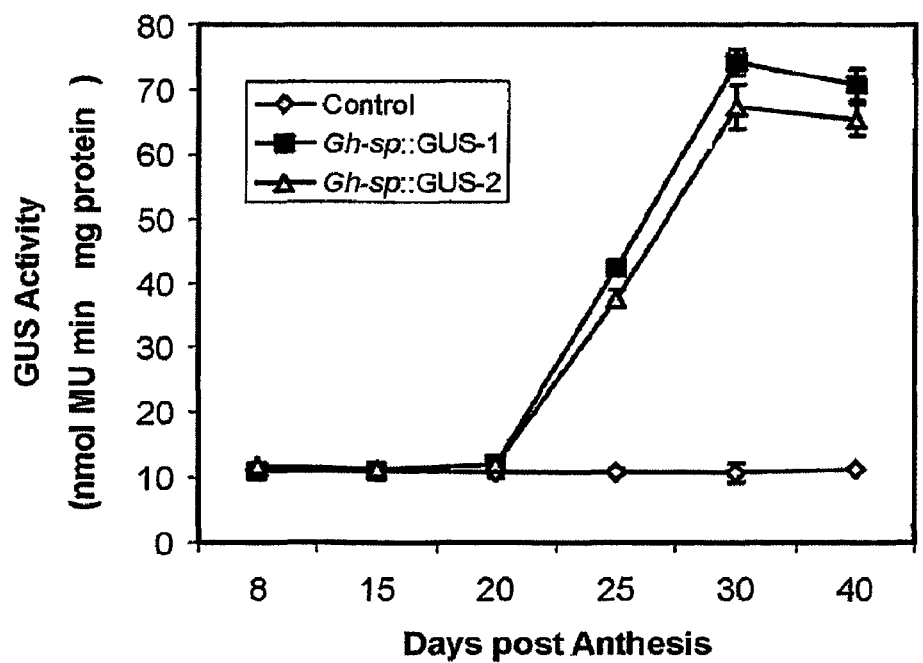
Figure 4

Control   Gh-rbcS::GUS-1

*GOSSYPIUM HIRSUTUM* TISSUE-SPECIFIC PROMOTERS AND THEIR USE

This application claims the priority benefit of U.S. Provisional Patent Application Ser. No. 60/223,496, filed Aug. 7, 2000, which is hereby incorporated by reference in its entirety.

FIELD OF THE INVENTION

The present invention relates to two tissue-specific promoters of cotton (*Gossypium hirsutum*) plants, their use in the assembly of DNA constructs which include a heterologous coding sequence under their control, and transgenic plants containing the DNA constructs.

BACKGROUND OF THE INVENTION

Genetic engineering of plants, which entails the isolation and manipulation of genetic material (usually in the form of DNA or RNA), and the subsequent introduction of that genetic material into plants or plant cells, offers considerable promise to modem agriculture and plant breeding. Increased crop values, higher yields, feed value, reduced production costs, pest resistance, stress tolerance, drought resistance, the production of pharmaceuticals, chemicals and biological molecules are all potentially available through genetic engineering techniques.

Methods for producing transgenic plants are well known. In a typical transformation scheme, a plant cell or plant tissue is transformed with a DNA construct, in which a "foreign" DNA molecule that is to be expressed in the plant cell or tissue is operably linked to a DNA promoter molecule, which will direct expression of the foreign DNA in the host cell, and to a 3' regulatory region of DNA that will allow proper processing of the RNA transcribed from the foreign DNA. The choice of foreign DNA to be expressed will be based on the trait, or effect, desired for the transformed plant. The promoter molecule is selected so that the foreign DNA is expressed in the desired plant. Promoters are regulatory sequences that determine the time and place of gene expression. Transcription of DNA is dependent upon the presence of a promoter which is a DNA sequence that directs the binding of RNA polymerase and thereby promotes mRNA synthesis.

Currently, the most widely used promoter for expression of foreign gene constructs in dicot plants is the cauliflower mosaic virus ("CaMV") 35S promoter (Ow et al., "Transient and Stable Expression of the Firefly Luciferase Gene in Plant Cells and Transgenic Plants," *Science* 234:856-859 (1986)). The CaMV 35S promoter provides strong constitutive expression in most dicot plants, including cotton. Other promoters that are widely used for inducing the expression of heterologous genes in transgenic plants include the nopaline synthase (NOS) gene promoter from *Agrobacterium tumefaciens* (U.S. Pat. No. 5,034,322 to Rogers et al.), the CaMV 19S promoter (U.S. Pat. No. 5,352,605 to Fraley et al.), promoters derived from any of the several actin genes, which are known to be expressed in most plant cell types (U.S. Pat. No. 6,002,068 to Privalle et al.), and the ubiquitin promoter, which affords heterologous gene expression in many cell types.

However, to develop transgenic cottons with specialized agronomic traits such as fiber quality and seed nutrition components, a larger arsenal of constitutive and tissue-specific promoters will be required. The characteristic expression patterns provided by these promoters must be analyzed in order to determine if they can be used to express beneficial genes in specific target tissues or developmental stages at maximum levels. Although such promoter tests can be conducted with transient expression assays or in model plant systems such as transgenic tobacco and Arabidopsis, gene expression analysis in stable transgenic cotton plants provides confirmation that these promoters can be used for the development of commercial transgenic cotton. While several fiber-specific promoters have been identified or otherwise tested in transgenic cotton plants (John and Crow, "Gene Expression in Cotton (*Gossypium hirsutum* L) Fiber: Cloning of the mRNAs," *Proc. Natl. Acad. Sci. U.S.A.* 89:5769-5773 (1992); Rinehart et al., "Tissue-specific and Developmental Regulation of Cotton Gene FbL2A," *Plant. Physiol.* 112(3):1331-1341 (1996); Dang et al., "Expression of a Cotton Fiber Gene Promoter in Tobacco," Proc. Beltwide Cotton Conf., San Antonio, Tex., Jan. 4-7, 1995 (Natl. Cotton Counc. Am., Memphis, Tenn.); Song et al., "Expression of a Promoter from a Fiber-specific Acyl Carrier Protein Gene in Transgenic Cotton Plants," Proc. Beltwide Cotton Conf., San Diego, Calif., Jan. 5-9, 1998 (Natl. Cotton Counc. Am., Memphis, Tenn.), other tissue-specific promoters would be desirable to afford different expression characteristics for foreign genes in transgenic plants.

The present invention overcomes these and other deficiencies in the art.

SUMMARY OF THE INVENTION

A first aspect of the present invention relates to an isolated DNA molecule selected from the group of: a promoter-effective DNA molecule of *Gossypium* which is operable in embryonic seed tissues; and a promoter-effective DNA molecule of *Gossypium* which is operable in chlorophyllous tissues.

A second aspect of the present invention relates to a chimeric gene including: a promoter region which includes a first DNA molecule that is a promoter region of the present invention; a coding region operably linked 3' to the promoter region, the coding region comprising a second DNA molecule encoding an mRNA molecule or a protein or polypeptide; and a 3' regulatory region operably linked 3' of the coding region. Expression systems, host cells, and transgenic plants and plant seeds which carry the chimeric gene of the invention are also disclosed.

A third aspect of the present invention relates to a method of making a transgenic plant including: transforming a plant cell or tissue with a chimeric gene of the present invention; and regenerating a transgenic plant from the transformed plant cell or tissue.

A fourth aspect of the present invention relates to a method of expressing a heterologous mRNA molecule or protein or polypeptide in chlorophyllous tissue of plants, said method including: transforming a plant cell or tissue with a chimeric gene of the present invention that contains a promoter-effective DNA molecule of *Gossypium* which is operable in chlorophyllous tissues; and regenerating a plant from the transformed plant cell or tissue, wherein expression of the mRNA molecule or protein or polypeptide occurs in chlorophyllous tissue of the plant.

A fifth aspect of the present invention relates to a method of expressing a heterologous mRNA molecule or protein or polypeptide in embryonic seed tissues including: providing a plant seed of the present invention which includes a chimeric gene containing a promoter-effective DNA molecule of *Gossypium* which is operable in embryonic seed tissues; and propagating the plant seed under conditions effective to yield a transgenic plant which expresses the mRNA molecule or the protein or polypeptide in embryonic seed tissues.

A sixth aspect of the present invention relates to a method of expressing a heterologous mRNA molecule or protein or polypeptide in chlorophyllous tissues including: providing a plant seed of the present invention which includes a chimeric gene containing a promoter-effective DNA molecule of *Gossypium* which is operable in chlorophyllous tissues; and propagating the plant seed under conditions effective to yield a transgenic plant which expresses the mRNA molecule or the protein or polypeptide in chlorophyllous tissues.

In the past few years, genetically modified cottons carrying insect and herbicide resistance genes have been successfully commercialized. Transgenic cottons are likely to play an increasingly important role in worldwide cotton production by conferring useful agronomic and fiber traits. The present invention identifies two promoters of *Gossypium* and their expression patterns. One directs seed-specific expression in transgenic plants (Gh-sp) and the other directs leaf-specific expression in transgenic plants (Gh-rbcS). Based on the patterns of GUS reporter gene expression under control of the promoters of the present invention in transgenic cotton, it is believed that chimeric genes which contain these promoters accurately reflect the expression of native genes. Thus, the present invention demonstrates that promoters from native cotton genes, when introduced into a chimeric gene, can effectively mimic the expression of endogenous genes and do not appear to be greatly affected by gene silencing.

BRIEF DESCRIPTION OF THE DRAWINGS

FIGS. 3A-B illustrate the seed-specific expression of the Gh-sp promoter of the present invention. Immature seeds 25 days post anthesis ("DPA") from non-transformed cotton plants (control, FIG. 3A) and a transgenic cotton plant containing a reporter gene construct with a promoter from a cotton seed protein gene (Gh-sp::GUS-1, FIG. 3B) were stained for β-glucuronidase ("GUS") activity. No detectable GUS activity was seen in control seeds (FIG. 3A). Embryos of seeds that contained the Gh-sp::GUS-1 reporter stained intensely blue with strongest signal in the cotyledons, indicating high levels of GUS activity in these organs (FIG. 3B).

FIG. 4 is a graph illustrating quantitative assays for GUS specific activity in extracts of developing ovules from untransformed cotton plants (control: ◇) and two independent transgenic cotton plants that contain the Gh-sp reporter gene construct (Gh-sp::GUS-1: ■, and Gh-sp::GUS-2: ▲). Background levels of GUS activity were seen in both control and transgenic plants through 20 DPA. A rapid increase in GUS activity occurred in transgenic seeds during the next 10 days of maturation, reaching maximum levels at about 30 DPA.

DETAILED DESCRIPTION OF THE INVENTION

Figure 1:
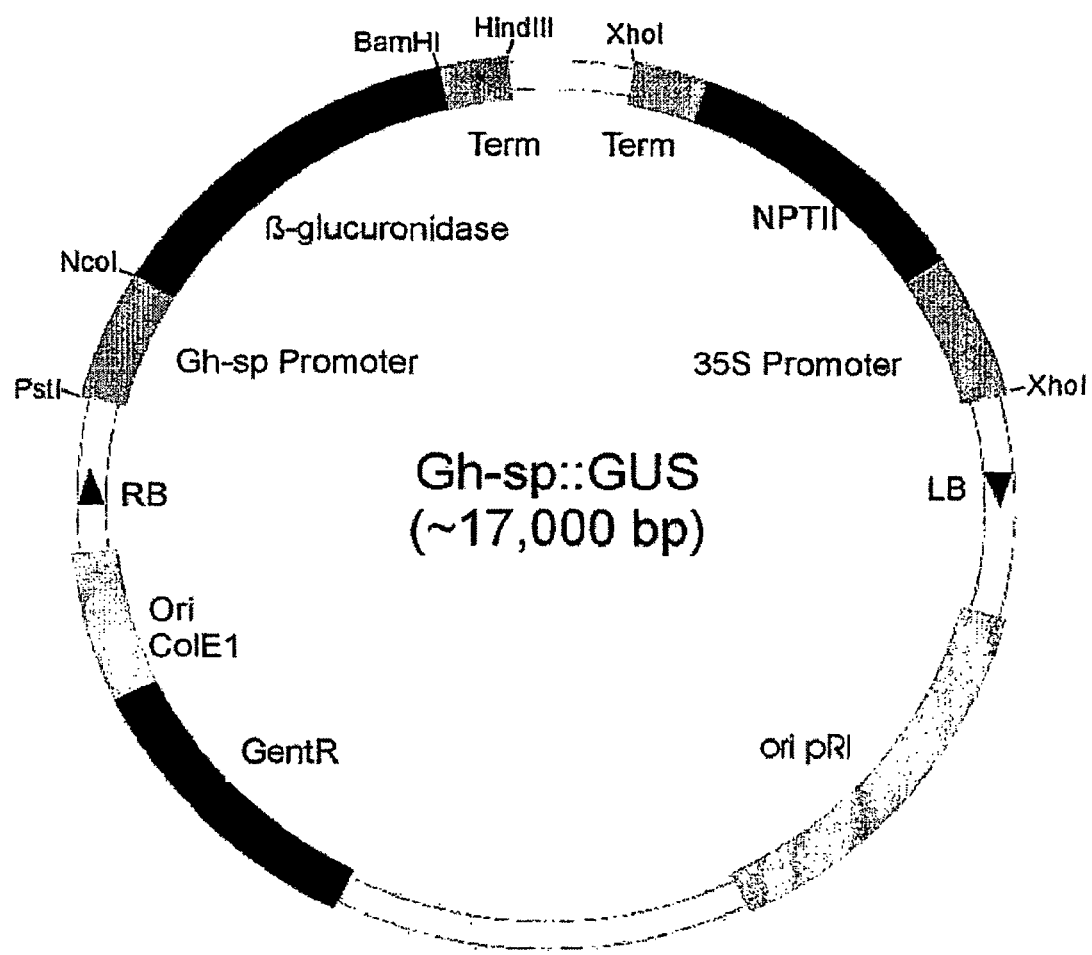
FIG. 1 is a map illustrating the structure of the Gh-sp::GUS construct, which was derived from the binary vector pCGN1578. The chimeric β-glucuronidase ("GUS") reporter gene includes the Gh-sp promoter ligated upstream of the GUS coding sequence and the CaMV 35S terminator fragment ligated downstream of the GUS coding sequence. (RB=right border, LB=left border, GentR is the gentamycin resistance gene, and NPTII is the neomycin transferase gene.)

This invention relates to a pair of *Gossypium*-derived DNA molecules which include promoter-effective DNA sequences for tissue-specific expression of native or foreign DNA molecules under their control.

A first *Gossypium* promoter is a DNA molecule which includes a promoter-effective DNA sequence that provides for expression of native or foreign DNA in chlorophyllous tissues of transgenic plants, preferably leaf tissue. According to one embodiment, the first *Gossypium* promoter is a *Gossypium hirsutum* promoter characterized by a nucleotide sequence according to SEQ ID No: 1 as follows:

```
cgctcatgtt aacaattaat tcctataatc gacatcaaaa ttatatgaaa gaattaacac    60
ttggttaccg agttaccata tttgaagata aggcgaaagg taaaaacaca aaaggcaagc   120
atgaccaagc aaacaaggta tggacataga ttttttttga atcgggaatg gccaaatggg   180
accgtgaaga ggggacaaag gagaaatcag gcattcacgg tttccattgg atgaaatgag   240
ataagatcac tgtgcttctt ccacgtggca ggttgccaaa agataaggct ttaccattca   300
agaaaagttt ccaccctctt tgtggtcata atggttgtaa tgtcatctga tttaaggatc   360
caacggtcac cctttctccc aaaccaatct ctaaatgttg tgaagcttag gccaaatttt   420
```

-continued

```
atgactatat ataggggatt gcaccaaggc agtgacacta ttaagggatc agtgagactc    480
ttttgtataa ctgtagcata tagtactagt aagcagtaat ag                      522
```

A second *Gossypium* promoter is a DNA molecule which includes a promoter-effective DNA sequence that provides for expression of native or foreign DNA in embryonic plant seed tissues, preferably cotyledon tissues. According to one embodiment, the second *Gossypium* promoter is a *Gossypium hirsutum* promoter characterized by a nucleotide sequence according to SEQ ID No: 2 as follows:

```
tttcagaacc aggtcgatag ttgaattagt tatgttattg gtccgactag tttgattaaa     60
aattattaaa aattcataaa ataagaatag aaaaatcgct ctaatcaagt tttttagttc    120
gacaagtacc aattcatgga tcaacctgct taacctcttg ttttggacaa tacctcaacc    180
gcttcttgat ccaatcggtt cggatcacta aaatacccct agaaggagat gaggctaagc    240
agagcgaaaa taacttttcca cgagacgaga atggaaacta ttgtatttaa atattttgat   300
tggattcaac aatcaatatt ttgtaaaggt aagtatttcc ataaactatt taagaataat    360
gattcttcat gtgcagaacg cggcggtact attttcaaga tacaatacat tactcgacgg    420
aacaattcgt attgcagtac caattatttt aaactgaatg aaatttagaa acacacaaga    480
aaaaaataat ataattataa aagtatcatt gtcttggaac tcagttctat attaattctc    540 attttggtg tttatatata gaatactaag aggtactgct tctttgaaaa gacacaacat    600
tttccttaga aaaaattatg aatagttata tatatttacg taaagacacc tctctttaat    660 tacattttc tttctttcct attatatata ttataaataa tataaaactt taatactata     720
tattttattt gaaattactt tataatatat aatataaatt atttatatgt tatatattat    780
atacaacaat tattagtaag ttaagattga atcagaaaaa atattacgag tcaaatagtt    840
ttttactttg ttttataata aaaaagtaat taaaataaat ttagccccaa taaaaaaaat    900
taaatctact ctttaggtga aatttttaat taattagtcc ctgaggtaag ctttcggctg    960
ctaagctatg aaattgtcat tatgtataac ttttatgcaa gtgtccctca cctctcggac   1020
acctccctcc ttcacaaaac agcgaggtgt acgctcacgt gtcaatgttg ggttacgtgt   1080
taaggctcca acattccgat ccaccggtca atccctctg tgtactctgt gtacataagc   1140
tgtgccccat atacaaacac caacggagct caacaaagta tctgtacggt accgcattat   1200
atttttattg accca                                                    1215
```

Fragments of the nucleotide sequence given as SEQ ID No: 1 or SEQ ID No: 2 which induce expression of heterologous DNA in transgenic plants are also suitable promoter DNA sequences for use in a chimeric gene of the present invention (infra). The fragments can be prepared by using PCR primers which direct cloning of a smaller portion of the nucleotide sequence of SEQ ID Nos: 1 or 2, and then PCR cloning the desired fragment and isolating the same. The fragment can be inserted into a chimeric gene and the chimeric gene tested to determine whether the fragment is a promoter-effective region. Efficacy of such fragments can be based on a comparison thereof with the full length SEQ ID Nos: 1 or 2.

This invention also relates to a chimeric gene which includes a promoter region including a first DNA molecule as described above; a coding region operably linked 3' to the promoter region, the coding region including a second DNA molecule encoding an mRNA molecule or a protein or polypeptide; and a 3' regulatory region operably linked 3' of the coding region.

The second DNA molecule is preferably heterologous DNA, which can encode any suitable heterologous RNA molecule (translatable, non-translatable, antisense, inhibitory RNA, etc.) or heterologous protein or polypeptide that confers to the transgenic plant containing the chimeric gene (or transgenic plant grown from a transgenic plant seed containing the chimeric gene) a desired trait. As used herein, the term "heterologous DNA" refers to a DNA segment that has been isolated or derived from one genotype, preferably amplified and/or chemically altered, and later introduced into a plant that may be a different genotype. Heterologous DNA does not generally include DNA of the same genotype, but "heterologous DNA" as used herein also includes DNA of the same genotype from which the amplified, chemically altered, or otherwise manipulated, DNA was first derived. Modification of the heterologous DNA sequence may occur, for example, by treating the DNA with a restriction enzyme to generate a DNA fragment which is capable of being operably linked to a promoter of the present invention. Modification can also occur by techniques such as site-directed mutagenesis or via PCR using primers designed to introduce a particular sequence, such as a restriction site. "Heterologous DNA" also includes DNA that is completely synthetic, semi-synthetic, or biologically derived, such as DNA derived from RNA. "Heterologous DNA" also includes, but is not limited to, non-plant genes such as those from bacteria, yeasts, animals, or viruses; modified genes, portions of genes, chimeric genes, as well as DNA that encodes for amino acids that are chemical precursors or biologics of commercial value, such as polymers or biopolymers. Pool et al., "In Search of the Plastic Potato," *Science* 245:1187-1189 (1989), which is hereby incorporated by reference in its entirety. Suitable heterologous DNA is any DNA for which expression in the chlorophyllous or embryonic seed tissue is beneficial to the plant or for which it is otherwise beneficial to have the DNA expressed selectively in the chlorophyllous or embryonic seed of the plant.

The heterologous RNA molecule or protein or polypeptide can be intended to modify a particular phenotype of the plant or, alternatively, the heterologous RNA molecule or protein or polypeptide can be substantially inert with respect to the plant, having its activity only when the plant tissue in which it is expressed is consumed by another organism.

With respect to heterologous proteins or polypeptides to be expressed in chlorophyllous tissues, suitable proteins or polypeptides encoded by the second DNA molecule can include, without limitation, an herbicide resistance protein or polypeptide such as phosphinothricin N-transferase (De Block, *EMBO J.* 6:2513 (1987), which is hereby incorporated by reference in its entirety), glyphosate resistance (EPSP synthase protein) (U.S. Pat. No. 4,535,060 to Comai et al., which is hereby incorporated by reference in its entirety), and chlorsulfuron resistance (Haughn et al., *Mol. Gen. Genet.* 211:266 (1988), which is hereby incorporated by reference in its entirety); a pest or pathogen resistance protein or polypeptide such as *Bacillus thuringiensis* toxin (U.S. Pat. No. 5,990,383 to Warren et al., which is hereby incorporated by reference in its entirety), crystal proteins (U.S. Pat. No. 4,996,155 to Sick et al., which is hereby incorporated by reference in its entirety), protease inhibitors (Ryan, *Annu. Rev. Phytopathol.* 38:425-449 (1990) and Mundy et al., *Planta* 169:51-63 (1986), each of which is hereby incorporated by reference in its entirety), chitinases and chitobiases (U.S. Pat. No. 5,290,687 to Suslow et al., U.S. Pat. No. 5,378,821 to Harman et al., and U.S. Pat. No. 5,446,138 to Blaiseu et al., each of which is hereby incorporated by reference in its entirety), lectins (EP Patent Application No. 351,924 A to Shell, which is hereby incorporated by reference in its entirety), lytic peptides (e.g., apidaceins, attacins, cecropins, caerulins, bombinins, lysozymes, magainins, melittins, sapecins, sarcotoxins, haloperoxidases, and xenopsins), and elicitors (e.g., defensins, elicitins, harpins) (U.S. Pat. No. 4,705,777 to Lehrer et al., U.S. Pat. No. 5,849,868 to Beer et al., U.S. Pat. No. 5,776,889 to Wei et al., U.S. Pat. No. 5,850,015 to Bauer et al., and U.S. Pat. No. 5,708,139 to Collmer et al., each of which is hereby incorporated by reference in its entirety); pathogen-derived proteins such as coat proteins and replicases (Beachy et al., *Rev. Phytopathol.* 28:451-474 (1990), WO 90/02184 to Gonsalves et al., U.S. Pat. No. 5,510,253 to Mitsky et al., and U.S. Pat. No. 5,503,999 to Jilka et al., each of which is hereby incorporated by reference in its entirety); vaccines and antibodies (Tavladorki et al., *Nature* 366:469 (1993), which is hereby incorporated by reference in its entirety); and enzymes of any source organism. Under control of the Gh-RbcS promoter, such proteins or polypeptides can be expressed selectively in the leaf, and to a lesser extent the stem, of the plant, and will not interfere with food crop or root system development.

With respect to heterologous RNA to be expressed in chlorophyllous tissues, suitable RNA molecules which are encoded by the second DNA molecule can include, without limitation, antisense delta-cadinene synthase RNA, and antisense plant virus RNA (e.g., for coat protein, replicase, etc.).

With respect to heterologous proteins or polypeptides to be expressed in embryonic seed tissues, suitable proteins or polypeptides encoded by the second DNA molecule can include, without limitation, a protein which modifies amino acid content in seed tissues (U.S. Pat. No. 5,559,223 to Falco et al., which is hereby incorporated by reference in its entirety), a protein which modifies fatty acid content of seed tissues, and a protein or polypeptide which modifies gossypol content. Other approaches include the use of plants as an alternative to petrochemicals. In that respect, the current emphasis is on increasing the production of lipids naturally produced by plants, and the need to increase the storage capacity of plants for useful products such as fatty acids and lipids. See U.S. Pat. No. 5,602,321 to Maliyakal, which is hereby incorporated by reference in its entirety. In certain circumstances, any of the above-identified proteins or polypeptides useful for expression in chlorophyllous tissues can also be expressed in embryonic seed tissues.

The DNA construct of the present invention also includes an operable 3' regulatory region, selected from among those which are capable of providing correct transcription termination and polyadenyation of mRNA for expression in plant cells, operably linked to the a DNA molecule which encodes for a protein of choice. A number of 3' regulatory regions are known to be operable in plants. Exemplary 3' regulatory regions include, without limitation, the nopaline synthase 3' regulatory region (Fraley, et al., "Expression of Bacterial Genes in Plant Cells," *Proc. Nat'l Acad. Sci. USA*, 80:4803-4807 (1983), which is hereby incorporated by reference in its entirety) and the cauliflower mosaic virus 3' regulatory region (Odell, et al., "Identification of DNA Sequences Required for Activity of the Cauliflower Mosaic Virus 35S Promoter," *Nature*, 313(6005):810-812 (1985), which is hereby incorporated by reference in its entirety). Virtually any 3' regulatory region known to be operable in plants would suffice for proper expression of the coding sequence of the DNA construct of the present invention.

The promoter region, the coding region, and the 3' regulatory region can be ligated together using well known molecular cloning techniques as described in Sambrook et al., *Molecular Cloning: A Laboratory Manual*, Second Edition, Cold Spring Harbor Press, NY (1989), which is hereby incorporated by reference in its entirety.

The DNA construct can also include a DNA molecule encoding a secretion signal. A number of suitable secretion signals are known in the art and others are continually being identified. The secretion signal can be a DNA leader which directs secretion of the subsequently translated protein or polypeptide, or the secretion signal can be an amino terminal peptide sequence that is recognized by a host plant secretory pathway. The secretion-signal encoding DNA molecule can be ligated between the promoter and the protein-encoding DNA molecule, using known molecular cloning techniques as described in Sambrook et al., *Molecular Cloning: A Laboratory Manual*, Second Edition, Cold Spring Harbor Press, N.Y. (1989), which is hereby incorporated by reference in its entirety.

A further aspect of the present invention includes an expression system that includes a suitable expression vector in which is inserted a chimeric gene of the present invention. In preparing the chimeric gene for expression, the various DNA sequences may normally be inserted or substituted into a bacterial plasmid. Any convenient plasmid may be employed, which will be characterized by having a bacterial replication system, a marker which allows for selection in a bacterium and generally one or more unique, conveniently located restriction sites. Numerous plasmids, referred to as transformation vectors, are available for plant transformation. The selection of a vector will depend on the preferred transformation technique and target species for transformation.

A variety of vectors are available for stable transformation using *Agrobacterium tumefaciens*, a soilborne bacterium that causes crown gall. Crown gall are characterized by tumors or galls that develop on the lower stem and main roots of the infected plant. These tumors are due to the transfer and incorporation of part of the bacterium plasmid DNA into the plant chromosomal DNA. This transfer DNA (T-DNA) is expressed along with the normal genes of the plant cell. The plasmid DNA, pTI, or Ti-DNA, for "tumor inducing plasmid," contains the vir genes necessary for movement of the T-DNA into the plant. The T-DNA carries genes that encode proteins involved in the biosynthesis of plant regulatory factors, and bacterial nutrients (opines). The T-DNA is delimited by two 25 bp imperfect direct repeat sequences called the "border sequences." By removing the oncogene and opine genes, and replacing them with a gene of interest, it is possible to transfer foreign DNA into the plant without the formation of tumors or the multiplication of *Agrobacterium tumefaciens*. Fraley, et al., "Expression of Bacterial Genes in Plant Cells," *Proc. Nat'l Acad. Sci.*, 80: 4803-4807 (1983), which is hereby incorporated by reference in its entirety.

Further improvement of this technique led to the development of the binary vector system. Bevan, M., "Binary *Agrobacterium* vectors for plant transformation," *Nucleic Acids Res.* 12:8711-8721 (1984), which is hereby incorporated by reference in its entirety. In this system, all the T-DNA sequences (including the borders) are removed from the pTi, and a second vector containing T-DNA is introduced into *Agrobacterium tumefaciens*. This second vector has the advantage of being replicable in *E. coli* as well as *A. tumefaciens*, and contains a multiclonal site that facilitates the cloning of a transgene. An example of a commonly used vector is pBin19. Frisch, et al., "Complete sequence of the binary vector Bin19," *Plant Molec. Biol.* 27:405-409 (1995), which is hereby incorporated by reference in its entirety. Any appropriate vectors now known or later described for plant transformation are suitable for use with the present invention.

U.S. Pat. No. 4,237,224 issued to Cohen and Boyer, which is hereby incorporated by reference in its entirety, describes the production of expression systems in the form of recombinant plasmids using restriction enzyme cleavage and ligation with DNA ligase. These recombinant plasmids are then introduced by means of transformation and replicated in unicellular cultures including procaryotic organisms and eukaryotic cells grown in tissue culture.

A further aspect of the present invention includes a host cell which includes a chimeric gene of the present invention. As described more fully hereinafter, the recombinant host cell can be either a bacterial cell (e.g., *Agrobacterium*) or a plant cell. In the case of recombinant plant cells, it is preferable that the chimeric gene is stably inserted into the genome of the recombinant plant cell.

The chimeric gene can be incorporated into cells using conventional recombinant DNA technology. Generally, this involves inserting the chimeric gene into an expression vector or system to which it is heterologous (i.e., not normally present). As described above, the chimeric gene contains the necessary elements for the transcription and translation in plant cells of the heterologous second DNA molecule.

Once the chimeric gene of the present invention has been prepared, it is ready to be incorporated into a host cell. Recombinant molecules can be introduced into cells via transformation, particularly transduction, conjugation, mobilization, or electroporation. The DNA sequences are cloned into the vector using standard cloning procedures in the art, as described by Sambrook et al., *Molecular Cloning: A Laboratory Manual*, Second Edition, Cold Springs Laboratory, Cold Springs Harbor, N.Y. (1989), which is hereby incorporated by reference in its entirety. Suitable host cells include, but are not limited to, bacteria, virus, yeast, mammalian cells, insect, plant, and the like. Preferably the host cells are either a bacterial cell or a plant cell.

Accordingly, another aspect of the present invention relates to a method of making a transgenic plant. Basically, this method is carried out by transforming a plant cell or tissue with a chimeric gene of the present invention and then regenerating a transgenic plant from the transformed plant cell or tissue. Preferably, the chimeric gene of the present invention is stably inserted into the genome of the recombinant plant cell(s) or tissue as a result of the transformation.

One approach to transforming plant cells with a chimeric gene of the present invention is particle bombardment (also known as biolistic transformation) of the host cell. This can be accomplished in one of several ways. The first involves propelling inert or biologically active particles at cells. This technique is disclosed in U.S. Pat. Nos. 4,945,050, 5,036,006, and 5,100,792, all to Sanford, et al., which are hereby incorporated by reference in their entirety. Generally, this procedure involves propelling inert or biologically active particles at the cells under conditions effective to penetrate the outer surface of the cell and to be incorporated within the interior thereof. When inert particles are utilized, the vector can be introduced into the cell by coating the particles with the vector containing the heterologous DNA. Alternatively, the target cell can be surrounded by the vector so that the vector is carried into the cell by the wake of the particle. Biologically active particles (e.g., dried bacterial cells containing the vector and heterologous DNA) can also be propelled into plant cells. Other variations of particle bombardment, now known or hereafter developed, can also be used.

Another method of introducing the chimeric gene of the present invention into a host cell is fusion of protoplasts with other entities, either minicells, cells, lysosomes, or other fusible lipid-surfaced bodies that contain the chimeric gene. Fraley, et al., *Proc. Natl. Acad. Sci. USA*, 79:1859-63 (1982), which is hereby incorporated by reference in its entirety.

The chimeric gene of the present invention may also be introduced into the plant cells by electroporation. Fromm, et al., *Proc. Natl. Acad. Sci. USA*, 82:5824 (1985), which is hereby incorporated by reference in its entirety. In this technique, plant protoplasts are electroporated in the presence of plasmids containing the DNA construct. Electrical impulses of high field strength reversibly permeabilize biomembranes allowing the introduction of the plasmids. Electroporated plant protoplasts reform the cell wall, divide, and regenerate.

Another method of introducing the chimeric gene into plant cells is to infect a plant cell with *Agrobacterium tumefaciens* or *Agrobacterium rhizogenes* previously transformed with the chimeric gene. Under appropriate conditions known in the art, the transformed plant cells or tissues are grown to form shoots or roots, and develop further into plants. Generally, this procedure involves inoculating the plant tissue with a suspension of bacteria and incubating the tissue for 48 to 72 hours on regeneration medium without antibiotics at 25-28° C.

*Agrobacterium* is a representative genus of the Gram-negative family Rhizobiaceae. Its species are responsible for crown gall (*A. tumefaciens*) and hairy root disease (*A. rhizogenes*). The plant cells in crown gall tumors and hairy roots are induced to produce amino acid derivatives known as opines, which are catabolized only by the bacteria. The bacterial genes responsible for expression of opines are a convenient source of control elements for chimeric expression cassettes. In addition, assaying for the presence of opines can be used to identify transformed tissue.

Heterologous genetic sequences such as a DNA construct of the present invention can be introduced into appropriate plant cells by means of the Ti plasmid of *A. tumefaciens* or the Ri plasmid of *A. rhizogenes*. The Ti or Ri plasmid is transmitted to plant cells on infection by *Agrobacterium* and is stably integrated into the plant genome. Schell, J., *Science*, 237:1176-83 (1987), which is hereby incorporated by reference in its entirety.

Plant tissue suitable for transformation include, but are not limited to leaf tissue, root tissue, meristems, zygotic and somatic embryos, megaspores and anthers.

After transformation, the transformed plant cells or tissues can be selected and whole plants regenerated.

Preferably, transformed cells are first identified using a selection marker simultaneously introduced into the host cells along with the chimeric gene of the present invention. Suitable selection markers include, without limitation, markers coding for antibiotic resistance, such as the nptII gene which confers kanamycin resistance (Fraley, et al., *Proc. Natl. Acad. Sci. USA*, 80:4803-4807 (1983), which is hereby incorporated by reference in its entirety) and the dhfr gene, which confers resistance to methotrexate (Bourouis et al., *EMBO J.* 2:1099-1104 (1983), which is hereby incorporated by reference in its entirety). A number of antibiotic-resistance markers are known in the art and others are continually being identified. Any known antibiotic-resistance marker can be used to transform and select transformed host cells in accordance with the present invention. Cells or tissues are grown on a selection media containing an antibiotic, whereby generally only those transformants expressing the antibiotic resistance marker continue to grow. Similarly, enzymes providing for production of a compound identifiable by color change are useful as selection markers, such as GUS (β-glucuronidase), or luminescence, such as luciferase.

Also suitable as selection markers for the present invention are genes that cause the overproduction of a plant product, such as the cytokinin-synthesizing ipt gene from *A. tumefaciens*. Localized over-production of cytokinin can be determined by known methods, such as ELISA assay. Hewelt et al., "Promoter Tagging with a Promoterless ipt Gene Leads to Cytokine-induced Phenotypic Variability in Transgenic Tobacco Plants: Implications of Gene Dosage Effects," *Plant J.* 6:879-91 (1994), which is hereby incorporated by reference in its entirety. The selection marker employed will depend on the target species; for certain target species, different antibiotics, herbicide, or biosynthesis selection markers are preferred.

Once a recombinant plant cell or tissue has been obtained, it is possible to regenerate a full-grown plant therefrom.

Plant regeneration from cultured protoplasts is described in Evans, et al., *Handbook of Plant Cell Cultures Vol.* 1: (MacMillan Publishing Co., New York, 1983); and Vasil I. R. (ed.), *Cell Culture and Somatic Cell Genetics of Plants*, Acad. Press, Orlando, Vol. I, 1984, and Vol. III (1986), which are hereby incorporated by reference in their entirety.

Means for regeneration vary from species to species of plants, but generally a suspension of transformed protoplasts or a petri plate containing transformed explants is first provided. Callus tissue is formed and shoots may be induced from callus and subsequently rooted. Alternatively, embryo formation can be induced in the callus tissue. These embryos germinate as natural embryos to form plants. The culture media will generally contain various amino acids and hormones, such as auxin and cytokinins. It is also advantageous to add glutamic acid and proline to the medium, especially for such species as corn and alfalfa. Efficient regeneration will depend on the medium, on the genotype, and on the history of the culture. If these three variables are controlled, then regeneration is usually reproducible and repeatable.

Thus, the present invention also relates to a transgenic plant which includes a chimeric gene of the present invention, preferably-stably transformed into the plant genome. According to one embodiment, the transgenic plant includes a chimeric gene of the present invention which contains a promoter-effective DNA molecule of *Gossypium* which is operable in embryonic seed tissues. According to a second embodiment, the transgenic plants includes a chimeric gene of the present invention which contains a promoter-effective DNA molecule of *Gossypium* which is operable in chlorophyllous tissues. According to another embodiment, the transgenic plant includes both type of chimeric genes of the present invention.

Exemplary plants of the present invention include, without limitation, all major species of rice, wheat, barley, rye, cotton, sunflower, peanut, corn, potato, sweet potato, bean, pea, chicory, lettuce, endive, cabbage, cauliflower, broccoli, turnip, radish, spinach, onion, garlic, eggplant, pepper, celery, carrot, squash, pumpkin, zucchini, cucumber, apple, pear, melon, strawberry, grape, raspberry, pineapple, soybean, tobacco, tomato, sorghum, sugarcane, and non-fruit bearing trees such as poplar, rubber, Paulownia, pine, and elm. It is known that practically all plants can be regenerated from cultured cells or tissues.

After the chimeric gene is stably incorporated in transgenic plants, it can be transferred to other plants by sexual crossing or by preparing cultivars. With respect to sexual crossing, any of a number of standard breeding techniques can be used depending upon the species to be crossed. Cultivars can be propagated in accord with common agricultural procedures known to those in the field.

Once transgenic plants of this type are produced, the plants themselves can be cultivated in accordance with conventional procedures.

Thus, a further aspect of the present invention relates to transgenic seeds recovered from the transgenic plants. The seeds can then be planted in the soil and cultivated using conventional procedures to produce transgenic plants.

Recovery of the product of expression of any heterologous DNA of choice used in the present invention will depend on the exact nature of the product, and the technique chosen for recovery will be known to those skilled in the art. Recovery of the heterologous RNA or heterologous protein or polypeptide, if desired, will depend on the nature of the promoter employed.

Thus, another aspect of the present invention relates to a method of expressing a heterologous mRNA molecule or protein or polypeptide in chlorophyllous tissue of plants. Basically, this approach is carried out by transforming a plant cell or tissue with a chimeric gene of the present invention which contains a promoter-effective DNA molecule of *Gossypium* which is operable in chlorophyllous tissues and then regenerating a plant from the transformed plant cell or tissue, wherein expression of the mRNA molecule or protein or polypeptide occurs in chlorophyllous tissue of the plant. Preferably, the promoter, while present in other plant tissues, affords substantially no expression of the mRNA or protein or polypeptide in non-chlorophyllous tissues of the plant. Transformation and regeneration can be performed as described above.

Alternatively, a method of expressing a heterologous mRNA molecule or protein or polypeptide in chlorophyllous tissues can be carried out by providing a plant seed which includes a chimeric gene containing a promoter-effective DNA molecule of *Gossypium* which is operable in chlorophyllous tissues and then propagating the plant seed under conditions effective to yield a transgenic plant which expresses the mRNA molecule or the protein or polypeptide in chlorophyllous tissues.

Still another aspect of the present invention relates to a method of expressing a heterologous mRNA molecule or protein or polypeptide in embryonic seed tissues. Basically, this approach is carried out by providing a plant seed which includes a chimeric gene containing a promoter-effective DNA molecule of *Gossypium* which is operable in embryonic seed tissues, and then propagating the plant seed under conditions effective to yield a transgenic plant which expresses the mRNA molecule or the protein or polypeptide in embryonic seed tissues. Propagating the plant seed can be carried out according to known growing procedures.

EXAMPLES

The following examples are provided to illustrate embodiments of the present invention, but they are by no means intended to limit its scope. The materials and methods described below were utilized in the following examples.

Plant Materials

Cotton plants (*Gossypium hirsutum* cv. Coker 312) were used for the source of genomic DNA and as a host for *Agrobacterium*-mediated transformation.

DNA Extraction

Genomic DNA was extracted from fully expanded leaf tissues using the procedure of Guillement et al. ("Isolation of Plant DNA: A Fast, Inexpensive, and Reliable Method," *Plant Mol. Biol. Rep.* 10(1):60-65 (1992), which is hereby incorporated by reference in its entirety) and further purified by phenol/chloroform/isoamyl alcohol (25:24:1) extraction and ethanol precipitation.

GUS Assay

Histochemical staining and fluorometric assays were used for the analysis of GUS expression (Jefferson, "Assaying Chimeric Genes in Plants: The GUS Gene Fusion System," *Plant Mol. Biol. Rep.* 5(2):387-405 (1987), which is hereby incorporated by reference in its entirety). Fresh tissues were used for the detection of GUS expression with histochemical staining solution (0.02 M 5-bromo-4-chloro-3-indolyl-β-D-glucuronide, 0.1 M $NaH_2PO_4$, 0.25 M EDTA. 5 mM potassium ferricyanide. 5 mM potassium ferrocyanide, 1.0% (v:v) Triton X-100, pH 7.0).

For the fluorometric assay, 0.2 g fresh tissues were ground in 500 μl GUS extraction buffer (50 mM phosphate buffer, pH 7.4, 10 mM β-mercaptoethanol, 10 mM EDTA. 0.1% sodium lauryl sarcosine, and 0.1% Triton X-100). The samples were centrifuged for 15 min at 4° C., 12,000×g. Ten microliters of supernatant was transferred in 0.5 ml GUS assay buffer (1 mM 4-methyl umbelliferyl β-D-glucuronide in extraction buffer). After incubation at 37° C. for 2 hours, the reactions were stopped by the addition of 2 ml of 0.2 M $Na_2CO_3$ and the fluorescence measured for with a Fluorometer (Turner Model 112). Three samples were taken from each individual plant and each sample was measured 3 times.

Example 1

Isolation of a Promoter from a Cotton Ribulose-1,5-Bisphosphate Carboxylase Small Unit Gene DNA sequences of a cotton ribulose-1,5-bisphosphate carboxylase small unit gene (Gh-rbcS) (GenBank accession number X54091, which is hereby incorporated by reference in its entirety) was identified. For PCR amplification of the 5' region of the Gh-rbcS gene, the following oligonucleotides were developed and used as 5' end and 3' end primers:

```
5' end primer                            (SEQ ID No: 3)
cgctcatgtt aacaattaat tcctataatc                   30

3' end primer                            (SEQ ID No: 4)
catcgtagta cgtgggtaag ctcgagtact                   30
```

About 1 μg of genomic DNA was used in 50 μl PCR reaction. PCR was performed with TaKaRA Ex Taq polymerase (Takara Shuzo Co., Ltd., Japan) under the conditions suggested by the manufacturer. PCR products were separated on 1.1% agarose gel and stained with ethidium bromide.

The resulting PCR product was then sequenced, identifying several discrepancies with the sequence reported at Genbank Accession No. X54091, which is hereby incorporated by reference in its entirety. The nucleotide sequence of the PCR product is as follows (SEQ ID No: 5), with the discrepancies indicated in bold typeface:

```
cggctcatgtt aacaattaat tcctataatc gacatcaaaa ttatatgaaa gaattaacac    60
ttggttaccg agttaccata tttgaagata aggcgaaagg taaaaacaca aaaggcaagc   120
atgaccaagc aaacaaggta tggacataga ttttttttga atcgggaatg gccaaatggg   180
accgtgaaga ggggacaaag gagaaatcag gcattcacgg tttccattgg atgaaatgag   240
ataagatcac tgtgcttctt ccacgtggca ggttgccaaa agataaggct ttaccattca   300
agaaaagttt ccaccctctt tgtggtcata atggttgtaa tgtcatctga tttaaggatc   360
```

-continued

```
caacggtcac cctttctccc aaaccaatct ctaaatgttg tgaagcttag gccaaatttt   420
atgactatat ataggggatt gcaccaaggc agtgacacta ttaagggatc agtgagactc   480
ttttgtataa ctgtagcata tagtactagt aagcagtaat agcaatggcc tcctccatga   540
tctcatcggc aaccattgcc accgtgaact gctcctcccc ggcacaggcc aacatggtgg   600
cccccttcac cggcctcaag tctgcctctg ctttcccagt cactaggaag gccaacaacg   660
acatcacttc tcttgcaagc aatggtggga gagtgcaatg catgcaggta cttggtgatg   720
cataaataca acttaaatta ccccaattgt ttgaacacaa caaattacat aaattgaatc   780
aaatatatat cttggctttt gagtataggt gtggcctcct cttgggaaga agaagttcga   840
gacactctca tacctccccg atcttacacc cgtacagttg gctaaggaag tagattacct   900
tcttcgctct aaatggattc cttgcttgga attcgaatta gaggtgtttt cgagctctaa   960
attattccat tccaacactt tatttttta gtgggatatt tgatttgatt aaatgtgttt   1020
tatatgtatg tgcaggaggg attcgtgcac cgtaagtact cgagcttacc cacgtactac   1080
gatg                                                                1084
```

PCR was used to amplify a sub-fragment from the above PCR product that included only the promoter and 5' flanking sequences. A 5' end primer was modified to include a PstI site (underlined below) and the 3' end primer was modified to include an NcoI site at the initiation codon (underlined below) as follows:

```
5'end primer                                   (SEQ ID No: 6)
ctgcagcgct catgttaaca attaattcct ataatc  36

3'end primer                                   (SEQ ID No: 7)
gagatcatgg aggaggccatggctattact g       31
```

Expected DNA fragments were cut from gels and subcloned into a TA cloning vector (pGEM-T system, Promega, Madison, Wis.). The subcloned PCR product was sequenced to verify its authenticity.

The nucleotide sequence of the subcloned PCR product is as follows (SEQ ID No: 8):

The PstI and NcoI restriction sites are underlined in SEQ ID No: 8 above. The promoter subfragment, therefore, includes nt 7-528 of SEQ ID No: 8, which is separately defined as SEQ ID No: 1.

Example 2

Isolation of a Promoter From a Cotton Seed Protein Gene

The DNA sequences of a seed protein gene (Gh-sp) (GenBank accession number M19389, which is hereby incorporated by reference in its entirety) was identified. For PCR amplification of the 5' region of the Gh-sp promoter, the following oligonucleotides were used as 5' and 3' end primers:

```
5'end primer                                   (SEQ ID No: 9)
gaaccaggtc gatagttgaa ttagttatgt t       31

3'end primer                                   (SEQ ID No: 10)
ctcagctgtt tgcatcatgg cagcatcttg         30
```

```
ctgcagcgct catgttaaca attaattcct ataatcgaca tcaaaattat atgaaagaat   60
taacacttgg ttaccgagtt accatatttg aagataaggc gaaaggtaaa aacacaaaag   120
gcaagcatga ccaagcaaac aaggtatgga catagattt ttttgaatcg gaatggcca    180 aatgggaccg tgaagagggg acaaaggaga atcaggcat tcacggttc cattggatga    240 aatgagataa gatcactgtg cttcttccac gtggcaggtt gccaaaagat aaggctttac   300
cattcaagaa aagtttccac cctctttgtg gtcataatgg ttgtaatgtc atctgattta   360
aggatccaac ggtcaccctt tctcccaaac caatctctaa atgttgtgaa gcttaggcca   420 aatttatga ctatatatag gggattgcac caaggcagtg acactattaa gggatcagtg   480
agactctttt gtataactgt agcatatagt actagtaagc agtaatagcc atggcctcct   540
ccatgatctc                                                         550
```

About 1 µg of genomic DNA was used in 50 µl PCR reaction. PCR was performed with TaKaRA Ex Taq polymerase (Takara Shuzo Co., Ltd., Japan) under the condition suggested by the manufacturer. PCR products were separated on 1.1% agarose gel and stained with ethidium bromide.

The resulting PCR product was sequenced, having a nucleotide sequence as follows (SEQ ID No: 11):

```
tttcagaacc aggtcgatag ttgaattagt tatgttattg gtccgactag tttgattaaa    60
aattattaaa aattcataaa ataagaatag aaaaatcgct ctaatcaagt tttttagttc   120
gacaagtacc aattcatgga tcaacctgct taacctcttg ttttggacaa tacctcaacc   180
gcttcttgat ccaatcggtt cggatcacta aaataccct agaaggagat gaggctaagc    240
agagcgaaaa taactttcca cgagacgaga atggaaacta ttgtatttaa atattttgat   300
tggattcaac aatcaatatt ttgtaaaggt aagtatttcc ataaactatt taagaataat   360
gattcttcat gtgcagaacg cggcggtact attttcaaga tacaatacat tactcgacgg   420
aacaattcgt attgcagtac caattatttt aaactgaatg aaatttagaa acacacaaga   460
aaaaaataat ataattataa agtatcatt gtcttggaac tcagttctat attaattctc    540
atttttggtg tttatatata gaatactaag aggtactgct tctttgaaaa gacacaacat   600
tttccttaga aaaaattatg aatagttata tatatttacg taaagacacc tctctttaat   660
tacattttc tttctttcct attatatata ttataaataa tataaaactt taatactata    720
atacaacaat tattagtaag ttaagattga atcagaaaaa atattacgag tcaaatagtt   840
ttttactttg ttttataata aaaaagtaat taaaataaat ttagccccaa taaaaaaaat   900
taaatctact ctttaggtga aatttttaat taattagtcc ctgaggtaag ctttcggctg   960
ctaagctatg aaattgtcat tatgtataac ttttatgcaa gtgtccctca cctctcggac  1020
acctccctcc ttcacaaaac agcgaggtgt acgctcacgt gtcaatgttg ggttacgtgt  1080
taaggctcca acattccgat ccaccggtca atcccctctg tgtactctgt gtacataagc  1140
tgtgccccat atacaaacac caacggagct caacaaagta tctgtacggt accgcattat  1200
atttttattg acccaccatg ggccagggac aacctaggag gcctcaacaa ccagcaggtc  1260
aaggtgagaa ccaagagcct atcaaatatg gagatgtttt caacgtcagc ggtgagttag  1320
ccaacaagcc tatcgcaccc caagatgcag ccatgatgca aacagctgag              1370
```

PCR was used to amplify a sub-fragment from the above PCR product that included only the promoter and 5' flanking sequences. A 5' end primer was modified to include a PstI site (underlined below) and the 3' end primer was modified to include an NcoI site at the initiation codon (underlined below) as follows:

```
5'end primer                                        (SEQ ID No: 12)
ctgcagtttc agaaccaggt cgatagttga                    30

3'end primer                                        (SEQ ID No: 13)
ctcctaggtt gtccctggcc catggtgggt caataaaaa          39
```

Expected DNA fragments were cut from gels and subcloned into a TA cloning vector (pGEM-T system, Promega, Madison, Wis.). The subcloned PCR product was sequenced to verify its authenticity.

The nucleotide sequence of the subcloned PCR product is as follows (SEQ ID No: 14):

```
ctgcagtttc agaaccaggt cgatagttga attagttatg ttattggtcc gactagtttg    60
attaaaaatt attaaaaatt cataaaataa gaatagaaaa atcgctctaa tcaagttttt   120
tagttcgaca agtaccaatt catggatcaa cctgcttaac ctcttgtttt ggacaatacc   180
tcaaccgctt cttgatccaa tcggttcgga tcactaaaat acccctagaa ggagatgagg   240
ctaagcagag cgaaaataac tttccacgag acgagaatgg aaactattgt atttaaatat   300
```

```
                                          -continued
tttgattgga ttcaacaatc aatattttgt aaaggtaagt atttccataa actatttaag    360
aataatgatt cttcatgtgc agaacgcggc ggtactattt tcaagataca atacattact    420
cgacggaaca attcgtattg cagtaccaat tattttaaac tgaatgaaat ttagaaacac    480
acaagaaaaa aataatataa ttataaaagt atcattgtct tggaactcag ttctatatta    540
attctcattt ttggtgttta tatatagaat actaagaggt actgcttctt tgaaaagaca    600
caacattttc cttagaaaaa attatgaata gttatatata tttacgtaaa gacacctctc    660
tttaattaca tttttctttc tttcctatta tatatattat aaataatata aaactttaat    720
actatatatt ttatttgaaa ttactttata atatataata taaattattt atatgttata    780
tattatatac aacaattatt agtaagttaa gattgaatca gaaaaaatat tacgagtcaa    840
atagtttttt actttgtttt ataataaaaa agtaattaaa ataaatttag ccccaataaa    900
aaaaattaaa tctactcttt aggtgaaatt tttaattaat tagtccctga ggtaagcttt    960
cggctgctaa gctatgaaat tgtcattatg tataacttttt atgcaagtgt ccctcacctc   1020
tcggacacct ccctccttca caaaacagcg aggtgtacgc tcacgtgtca atgttgggtt   1080
acgtgttaag gctccaacat tccgatccac cggtcaatcc cctctgtgta ctctgtgtac   1140
ataagctgtg ccccatatac aaacaccaac ggagctcaac aaagtatctg tacggtaccg   1200
cattatattt ttattgaccc accatgggcc agggacaacc taggag                  1246
```

The PstI and NcoI restriction sites are underlined in SEQ ID No: 14 above. The promoter subfragment, therefore, includes nt 7-1221 of SEQ ID No: 14, which is separately defined as SEQ ID No: 2.

Sequence analysis of the Gh-sp promoter indicated that it contains a conserved sequence motif located 89 bp upstream of TATA box that is similar to the G-box core motif (ACGT). Similar elements are required for seed-specific gene expression in several plant species (Salberg et al., "Deletion Analysis of a 2S Seed Storage Protein Promoter of *Brassica napus* in Transgenic Tobacco," *Plant Mol. Biol.* 23(4):671-683 (1993); Vincentz et al., "ACGT and Vicilin Core Sequence in a Promoter Domain Required for Seed-specific Expression of a 2S Storage Protein Gene are Recognized by the Opaque-2 Regulatory Protein," *Plant Mol. Biol.* 34(6):879-889 (1997); Wu et al., "The GCN4 Motif in a Rice Glutelin Gene is Essential for Endosperm-specific Gene Expression and is Activated by Opaque-2 in Transgenic Rice Plants," *Plant J.* 14(6):673-683 (1998), which are hereby incorporated by reference in their entirety).

Example 3

Figure 2:
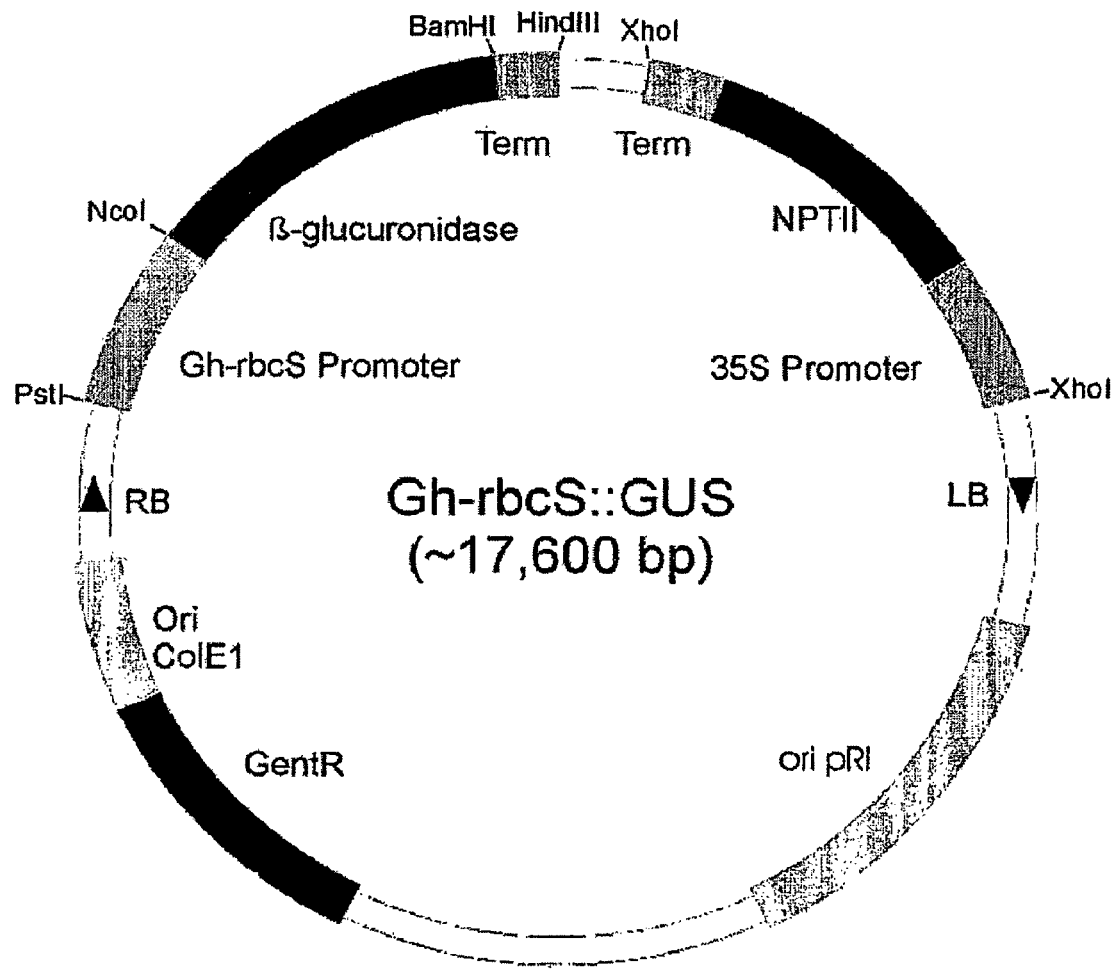
FIG. 2 is a map illustrating the structure of the Gh-rbcS::GUS construct, which was derived from the binary vector pCGN1578. The chimeric GUS reporter gene includes the Gh-rbcS promoter ligated upstream of the GUS coding sequence and the CaMV 35S terminator fragment ligated downstream of the GUS coding sequence. (RB=right border, LB=left border, GentR is the gentamycin resistance gene, and NPTII is the neomycin transferase gene.)

Construction of Chimeric GUS Genes Using Gh-rbcS and Gh-sp Promoters and Preparation of *Agrobacterium* Expression Vector In order to build gene constructs including either a Gh-rbcS or a Gh-sp promoter in a GUS reporter gene, PstI sites were added to the 5' ends of the promoter sequences and the initiation codons were mutated to NcoI sites. This was done by PCR amplification of the subcloned promoter fragments with primers containing the respective restriction sites and the resulting PCR products were purified and digested with PstI and NcoI. This resulted in a 1215 bp fragment containing the Gh-sp promoter and a 522 bp fragment containing the Gh-rbcS promoter. Each of these two promoter fragments were separately ligated into the binary vector pCGN1578 along with a fragment containing the β-glucuronidase (GUS) reporter gene and the CaMV 35S terminator fragment. These two resulting gene cassettes, Gh-sp::GUS and Gh-rbcS::GUS, are illustrated in FIGS. 1 and 2, respectively. These constructs were introduced into the disarmed *Agrobacterium tumefaciens* strain EHA101 for cotton transformation.

Example 4

Preparation of Transgenic Cotton Plants Expressing Chimeric GUS Gene Gh-sp::GUS

Transformation of cotton plants with a Gh-sp::GUS gene construct was carried out by inoculation of hypocotyl segments of cotton (cv. Coker 312) seedlings with *Agrobacterium tumefaciens* and regeneration of plants via somatic embryogenesis as previously reported (Bayley et al., "Engineering 2,4-D resistance into cotton," *Theor. Appl. Genet.* 83(3):645-662 (1992); Payton et al., "Over-expression of Chloroplast-targeted Mn Superoxide Dismutase in Cotton (*Gossypium hirsutum* L., cv. Coker 312) Does Not Alter the Reduction of Photosynthesis After Short Exposures to Low Temperature and High Light Intensity," *Photosynthesis Res.* 52:233-244 (1997), which are hereby incorporated by reference in their entirety).

Cotton plants were regenerated from two independent cell lines transformed with the Gh-sp::GUS gene construct. The presence of the GUS reporter gene in these transgenic plants was confirmed by PCR amplification. These plants were grown to flowering in a greenhouse and analyzed for GUS expression. Different plant tissues including sections of emerging leaves, longitudinal section of shoots, roots, petals, mature anthers, and styles were stained for GUS activity. After incubation in the staining solution for 16 hours at 37°

C., no blue stain was apparent in any tissues from these primary transgenic (T$_0$) plants indicating that the GUS gene was not expressed.

To determine the expression pattern of Gh-sp promoter in seed development, bolls from the T$_0$ plants were tagged and ovules were harvested at different days post anthesis (DPA) and subsequently stained for GUS expression. GUS activity was not detected in developing seeds before 25 DPA, but very strong staining was observed in the developing seeds at 30 DPA or later (FIG. 3B). Staining was limited to embryonic tissues with strongest activity in the cotyledons. Results from quantitative fluorometric assays of GUS activity matched the histochemical staining pattern in maturing seeds. GUS activity in ovule extracts increased dramatically from background levels at 25 DPA (FIG. 4).

The promoter sequence used in this experiment is from the late embryogenesis abundant (Lea) class of seed protein gene (Baker et al., "Sequence and Characterization of 6 Lea Protein and Their Genes from Cotton," *Plant Mol. Biol.* 11(2): 277-291 (1988), which is hereby incorporated by reference in its entirety). Generally, water loss during late seed formation triggers the expression of Lea genes in all higher plants that produce desiccated seeds. Study of the developmental and environmental induction of Lea genes in cotton indicated that most Lea mRNAs started to accumulate in 30 DPA developing seeds (Hughes and Galau, "Developmental and environmental induction of Lea and LeaA mRNAs and the postabscission program during embryo culture," Plant Cell 3(6): 605-618 (1991), which is hereby incorporated by reference in its entirety). Therefore, the GUS expression pattern controlled by Gh-sp promoter in transgenic cotton plants was similar to that of the endogenous cotton Lea genes. This seed specific-promoter will be useful in the genetic modification of seed properties such as protein quality, fatty acid composition, and gossypol content.

Example 5

Preparation of Transgenic Cotton Plants Expressing Chimeric GUS Gene Gh-rbcS::GUS Transformation of cotton plants with the Gh-rbcS::GUS gene constructs was carried out by inoculation of hypocotyl segments of cotton (cv. Coker 312) seedlings with *Agrobacterium tumefaciens* and regeneration of plant via somatic embryogenesis as previously reported (Bayley et al., "Engineering 2,4-D resistance into cotton," *Theor. Appl. Genet.* 83(3):645-662 (1992); Payton et al., "Over-expression of Chloroplast-targeted Mn Superoxide Dismutase in Cotton (*Gossypium hirsutum* L., cv. Coker 312) Does Not Alter the Reduction of Photosynthesis After Short Exposures to Low Temperature and High Light Intensity," *Photosynthesis Res.* 52:233-244 (1997), which are hereby incorporated by reference in their entirety).

The small subunit of ribulose-1,5-bisphosphate carboxylase (rbcS) is encoded by gene families in most plants. Promoters from one group of these genes contain two cis-acting elements, the I-box and the G-box, that are important for their tissue-specific expression (Donald and Cashmore, "Mutation of Either G box or I box Sequences Profoundly Affects Expression from the Arabidopsis rbcS-1A Promoter," *EMBO J.* 9(3):1717-1726 (1990); Manzara et al., "Developmental and Organ-specific Changes in Promoter DNA-protein Interactions in Tomato rbcS Gene Family," *Plant Cell* 3(3):1305-1316 (1991), which are hereby incorporated by reference in their entirety). Analysis of transgenic tomato plants expressing a rbcS-promoter::GUS fusion gene confirmed that promoter fragments ranging from 0.6 to 3.0 kb of rbcS1, rbcS2, and rbcS3A genes were sufficient to confer the temporal and organ-specific expression pattern (Manzara et al., "Developmental and Organ-specific Changes in DNA-protein Interactions in the Tomato rbcS1, rbcS2 and rbcS3 Promoter Regions," *Plant Mol. Biol.* 21(1):69-88 (1993); Meier et al., "Organ-specific Differential Regulation of a Promoter Subfamily for the Ribulose-1,5-bisphosphate Carboxylase/Oxygenase Small Subunit Genes in Tomato," *Plant Physiol.* 107 (3):1105-1118 (1995), which are hereby incorporated by reference in their entirety). In these genes, the I-box and G-box are located within the region from −600 bp to −100 upstream of transcription initiation site. The 522 bp promoter fragment from cotton rbcS gene that was used to develop the GUS reporter gene construct reported here does include putative I-box (nt 234-247 in SEQ ID No: 1) and G-box (nt 261-269 in SEQ ID No: 1) sequences upstream of the start codon.

Figure 5:
FIG. 5 is an image illustrating segments of expanding leaves from non-transformed (Control) cotton plants and transgenic cotton plants that contained a reporter gene with a promoter from a cotton rbcS gene (Gh-rbcS::GUS-1). The expanding leaves were stained for GUS activity. While GUS activity was not detected in leaves of control plants, leaves from the transgenic plant stained intensely blue indicating high levels of GUS activity.
Figure 6:
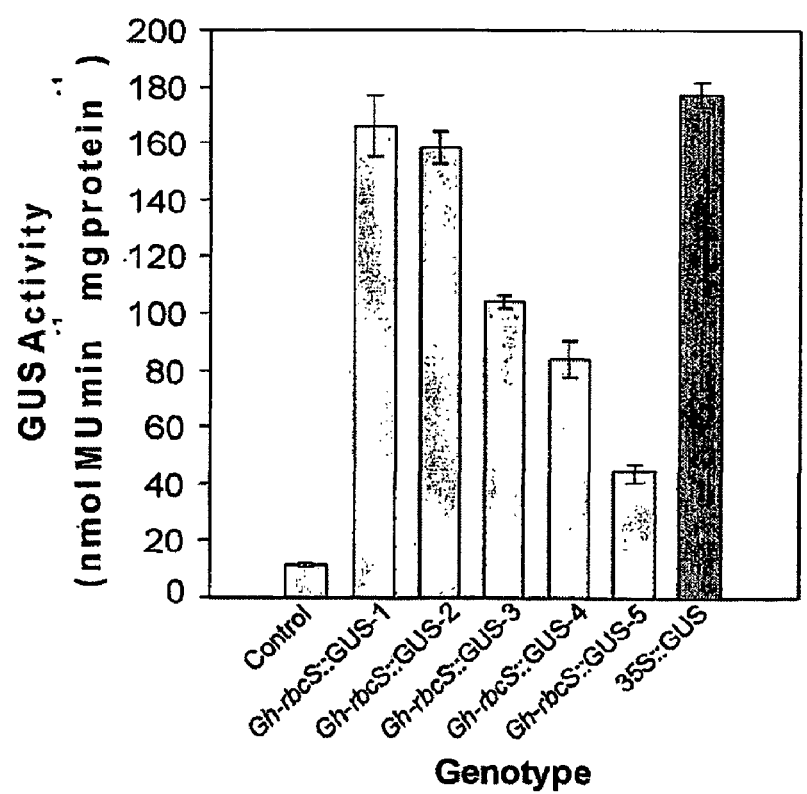
FIG. 6 is a graph illustrating quantitative assays of GUS specific activity in extracts from expanding leaves from untransformed plants (Control) cotton plants and five independent transgenic cotton plants containing the Gh-rbcS::GUS transgenic cotton plant containing a GUS reporter gene controlled by a CaMV 35S promoter (35S::GUS). Levels of GUS activity in all of the Gh13::GUS plants were substantially higher than in control plants but activity varied by as much as 300% between transgenic lines. The two highest expressing plants (Gh-rbcS::GUS-1 and Gh-rbcS::GUS-2) had activities similar to those in leaves of a typical 35S::GUS containing plants.

Transgenic cotton plants were regenerated from 5 independent cell lines transformed with the Gh-rbcS::GUS gene cassette and the presence of the GUS fragment was confirmed in these plants by PCR amplification of genomic DNA. Leaf segments from emerging leaves of plants with 4-5 true leaves and flowering plants were incubated with GUS staining solution at 37° C. overnight. GUS expression was detected in all 15 transgenic plants tested and no blue color appeared in non-transgenic plants (FIGS. 5 and 6). Other tissues including roots from regenerated transgenic plantlets, longitudinal sections of shoot, petal, anthers, and 8 DPA developing ovules from flowering transgenic plants were tested for GUS expression. GUS activity was not detected in these samples except for the shoot, which showed light staining. These results demonstrate the GUS gene expression under control of the Gh-rbcS promoter is expressed in chlorophyll-containing tissues, primarily the leaves.

Fluorometric assay of leaf tissues indicated that GUS activity in leaves of Gh-rbcS::GUS transgenic plants was significantly higher than non-transgenic plants and transgenic plants without the GUS reporter gene. There was considerable variation in the level of GUS expression among transgenic plants regenerated from different cell lines (FIG. 6). This is could be caused by "position effects" that depend on the chromosomal location of the transgene insertion or by co-suppression that is often associated with the presence of multiple transgene inserts. Expression in transgenic cotton plants with the highest levels of GUS activity (Gh-rbcS::GUS-1 and Gh-rbcS::GUS-2) were only slightly lower than that of a 35S::GUS transgenic plant that was also tested. A tobacco tissue-specific rbcS gene promoter has been successfully used to generate herbicide resistant transgenic plants (Stalker et al., "Herbicide Resistance in Transgenic Plants Expressing a Bacterial Detoxification Gene," *Science* 242 (4877):419-423 (1988), which is hereby incorporated by reference in its entirety). Based on the GUS expression from this experiment, Gh-rbcS promoter could be used to express foreign genes at high levels in green tissues of transgenic cotton plants.

Although the invention has been described in detail for the purpose of illustration, it is understood that such detail is solely for that purpose, and variations can be made therein by those skilled in the art without departing from the spirit and scope of the invention which is defined by the following claims.

What is claimed is:

1. An isolated DNA molecule consisting of a seed-specific promoter-effective DNA molecule of *Gossypium* which is non-constitutive and operable predominantly in cotyledon tissue, wherein the isolated DNA molecule consists of the nucleotide sequence of SEQ ID No: 2.

2. A chimeric gene comprising:
   a promoter region comprising a first DNA molecule according to claim 1,
   a heterologous coding region operably linked 3' to the promoter region,
   The heterologous coding region comprising a second DNA molecule encoding an mRNA molecule or a protein or polypeptide; and
   a 3' regulatory region operably linked 3' of the coding region.

3. the chimeric gene according to claim 2, wherein the second DNA molecule encodes a protein or polypeptide selected from the group consisting of a protein which modifies amino acid content in seed tissues, a protein which modifies fatty acid content of seed tissues, and protein or polypeptide which modifies gossypol content.

4. An expression system comprising an expression vector in which is inserted a chimeric gene according to claim 2.

5. A host cell comprising a chimeric gene according to claim 2.

6. The host cell according to claim 5, wherein the host cell is a plant cell or a bacteria cell.

7. The host cell according to claim 6, wherein the bacteria cell is *Agrobacterium*.

8. The host cell according to claim 6, wherein the plant cell is a cell of a plant selected from the group consisting of rice, wheat, barley, rye, cotton, sunflower, peanut, corn, potato, sweet potato, bean, pea, chicory, lettuce, endive, cabbage, cauliflower, broccoli, turnip, radish, spinach, onion, garlic, eggplant, pepper, celery, carrot, squash, pumpkin, zucchini, cucumber, apple, pear, melon, strawberry, grape, raspberry, pineapple, soybean, tobacco, tomato, sorghum, sugarcane, poplar, rubber, Paulownia, pine, and elm.

9. A transgenic plant comprising a chimeric gene according to claim 2.

10. The transgenic plant according to claim 9, wherein the second DNA molecule encodes a protein or polypeptide selected from the group consisting of a protein which modifies amino acid content in seed tissues, a protein which modifies fatty acid content of seed tissues, and protein or polypeptide which modifies gossypol content.

11. The transgenic plant according to claim 9, wherein the plant is selected from the group consisting of rice, wheat, barley, rye, cotton, sunflower, peanut, corn, potato, sweet potato, bean, pea, chicory, lettuce, endive, cabbage, cauliflower, broccoli, turnip, radish, spinach, onion, garlic, eggplant, pepper, celery, carrot, squash, pumpkin, zucchini, cucumber, apple, pear, melon, strawberry, grape, raspberry, pineapple, soybean, tobacco, tomato, sorghum, sugarcane, poplar, rubber, Paulownia, pine, and elm.

12. The transgenic plant according to claim 9, wherein the plant is a cotton plant.

13. A plant seed obtained from the transgenic plant of claim 9,
    wherein the plant seed comprises the chimeric gene.

14. the plant seed according to claim 13, wherein the transgenic plant is selected from the group consisting of rice, what, barley, rye, cotton, sunflower, peanut, corn, potato, sweet potato, bean, pea chicory, lettuce, endive, cabbage, cauliflower, broccoli, turnip, radish, spinach, onion, garlic, eggplant, pepper, celery, carrot, squash, pumpkin, zucchini, cucumber, apple, pear, melon, strawberry, grape, raspberry, pineapple, soybean, tobacco, tomato, sorghum, sugarcane, poplar, rubber, Paulownia, pine, and elm.

15. The plant seed according to claim 13, wherein the transgenic plant is cotton.

16. A transgenic plant seed comprising a chimeric gene according to claim 2.

17. The transgenic plant seed according to claim 16, wherein the embryonic seed tissue is a cotyledon.

18. The transgenic plant seed according to claim 16, wherein the second DNA molecule encodes a protein or polypeptide selected from the group consisting of a protein which modifies amino acid content in seed tissues, a protein which modifies fatty acid content of seed tissues, and a protein or polypeptide which modifies gossypol content.

19. The transgenic plant seed according to claim 16, wherein the transgenic plant seed is from a plant selected from the group consisting of rice, wheat barley, rye, cotton, sunflower, peanut, corn, potato, sweet potato, bean, pea, chicory, lettuce, endive, cabbage, cauliflower, broccoli, turnip, radish, spinach, onion, garlic eggplant, pepper, celery, carrot, squash, pumpkin, zucchini, cucumber, apple pear, melon, strawberry, grape, raspberry, pineapple, soybean, tobacco, tomato, sorghum, sugarcane, poplar, rubber Paulownia, pine and elm.

20. The transgenic plant seed according to claim 16, wherein the transgenic plant seed is from a cotton plant.

21. a method of making a transgenic plant comprising:
    transforming a plant cell or tissue with a chimeric gene according to claim 2, and
    regenerating a transgenic plant from the transformed plant cell or tissue.

22. The method according to claim 21, wherein said transforming is carried out under conditions effective to insert the chimeric gene into the genome of the transformed plant cell or tissue.

23. The method according to claim 21, wherein said transforming comprises:
    propelling particles at a plant cell under conditions effective for the particles to penetrate into the cell interior and introducing an expression vector comprising the chimeric gene into the plant cell interior.

24. The method according to claim 21, wherein said transforming comprises:
    propelling particles at a plant cell under conditions effective for the particles to penetrate into the cell interior and introducing an expression vector comprising the chimeric gene into the plant cell interior.

25. A method of expressing a heterologous mRNA molecule or protein or polypeptide in embryonic seed tissues comprising:
    providing a plant seed according to claim 16 and
    propagating the plant seed under conditions effective to yield a transgenic plant which expresses the mRNA molecule or the protein or polypeptide in embryonic seed tissues.

26. The method according to claim 25, wherein the embryonic seed tissue is a cotyledon.

27. An isolated DNA molecule consisting of the nucleotide sequence of SEQ ID No. 2.

28. A chimeric gene comprising:
    a promoter region consisting of a first DNA molecule according to claim 27
    a coding region operably linked 3' of the coding region.

29. An expression system comprising an expression vector in which is inserted a chimeric gene according to claim 28.

30. A host cell comprising a chimeric gene according to claim 28.

31. A transgenic plant comprising a chimeric gene according to claim 28.

32. A transgenic plant seed comprising a chimeric gene according to claim 28.

33. A method of making a transgenic plant comprising;
    transforming a plant cell or tissue with a chimeric gene according to claim 28; and
    regenerating a transgenic plant from the transformed plant cell or tissue.

34. A method of expressing a heterologous mRNA molecule or protein or polypeptide in embryonic seed tissues comprising:
    providing plant seed according to claim 32 and
    propagating the plant seed under conditions effective to yield a transgenic plant which expresses the mRNA molecule or the protein or polypeptide in embryonic seed tissues.

35. The isolated DNA molecule according to claim 1, wherein the DNA molecule, when present in a transgene introduced into *Gossypium*, is effective to induce expression of a product encoded by the transgene in embryonic seed tissue at about 25 days post anthesis.

* * * * *

SEQUENCE LISTING

<160> NUMBER OF SEQ ID NOS: 14

<210> SEQ ID NO 1
<211> LENGTH: 522
<212> TYPE: DNA
<213> ORGANISM: Gossypium hirsutum

<400> SEQUENCE: 1

```
cgctcatgtt aacaattaat tcctataatc gacatcaaaa ttatatgaaa gaattaacac      60
ttggttaccg agttaccata tttgaagata aggcgaaagg taaaaacaca aaaggcaagc     120
atgaccaagc aaacaaggta tggacataga ttttttttga atcgggaatg gccaaatggg     180
accgtgaaga ggggacaaag gagaaatcag gcattcacgg tttccattgg atgaaatgag     240
ataagatcac tgtgcttctt ccacgtggca ggttgccaaa agataaggct ttaccattca     300
agaaaagttt ccaccctctt tgtggtcata atggttgtaa tgtcatctga tttaaggatc     360
caacggtcac cctttctccc aaaccaatct ctaaatgttg tgaagcttag gccaaatttt     420
atgactatat atagggggatt gcaccaaggc agtgacacta ttaagggatc agtgagactc     480
ttttgtataa ctgtagcata tagtactagt aagcagtaat ag                        522
```

<210> SEQ ID NO 2
<211> LENGTH: 1215
<212> TYPE: DNA
<213> ORGANISM: Gossypium hirsutum

<400> SEQUENCE: 2

```
tttcagaacc aggtcgatag ttgaattagt tatgttattg gtccgactag tttgattaaa      60
aattattaaa aattcataaa ataagaatag aaaaatcgct ctaatcaagt tttttagttc     120
gacaagtacc aattcatgga tcaacctgct taacctcttg ttttggacaa tacctcaacc     180
gcttcttgat ccaatcggtt cggatcacta aaatacccct agaaggagat gaggctaagc     240
agagcgaaaa taactttcca cgagacgaga atggaaacta ttgtatttaa atattttgat     300
tggattcaac aatcaatatt ttgtaaaggt aagtatttcc ataaactatt taagaataat     360
gattcttcat gtgcagaacg cggcggtact attttcaaga tacaatacat tactcgacgg     420
aacaattcgt attgcagtac caattatttt aaactgaatg aaatttagaa acacacaaga     480
aaaaaataat ataattataa aagtatcatt gtcttggaac tcagttctat attaattctc     540
attttttggtg tttatatata gaatactaag aggtactgct tctttgaaaa gacacaacat     600
tttccttaga aaaaattatg aatagttata tatatttacg taaagacacc tctctttaat     660
tacatttttc tttctttcct attatatata ttataaataa tataaaactt taatactata     720
tattttattt gaaattactt tataatatat aatataaatt atttatatgt tatatattat     780
atacaacaat tattagtaag ttaagattga atcagaaaaa atattacgag tcaaatagtt     840
ttttactttg ttttataata aaaagtaat taaaataaat ttagccccaa taaaaaaaat     900
taaatctact cttaggtgaa aattttttaat taattagtcc ctgaggtaag ctttcggctg     960
ctaagctatg aaattgtcat tatgtataac ttttatgcaa gtgtccctca cctctcggac    1020
acctccctcc ttcacaaaac agcgaggtgt acgctcacgt gtcaatgttg ggttacgtgt    1080
taaggctcca acattccgat ccaccggtca atcccctctg tgtactctgt gtacataagc    1140
tgtgccccat atacaaacac caacggagct caacaaagta tctgtacggt accgcattat    1200
atttttattg accca                                                    1215
```

<210> SEQ ID NO 3
<211> LENGTH: 30
<212> TYPE: DNA
<213> ORGANISM: Artificial Sequence
<220> FEATURE:
<223> OTHER INFORMATION: Description of Artificial Sequence: primer

<400> SEQUENCE: 3
cgctcatgtt aacaattaat tcctataatc                              30

<210> SEQ ID NO 4
<211> LENGTH: 30
<212> TYPE: DNA
<213> ORGANISM: Artificial Sequence
<220> FEATURE:
<223> OTHER INFORMATION: Description of Artificial Sequence: primer

<400> SEQUENCE: 4
catcgtagta cgtgggtaag ctcgagtact                              30

<210> SEQ ID NO 5
<211> LENGTH: 1084
<212> TYPE: DNA
<213> ORGANISM: Gossypium hirsutum

<400> SEQUENCE: 5
cgctcatgtt aacaattaat tcctataatc gacatcaaaa ttatatgaaa gaattaacac    60
ttggttaccg agttaccata tttgaagata aggcgaaagg taaaaacaca aaaggcaagc   120
atgaccaagc aaacaaggta tggacataga ttttttttga atcgggaatg gccaaatggg   180
accgtgaaga ggggacaaag gagaaatcag gcattcacgg tttccattgg atgaaatgag   240
ataagatcac tgtgcttctt ccacgtggca ggttgccaaa agataaggct ttaccattca   300
agaaaagttt ccaccctctt tgtggtcata atggttgtaa tgtcatctga tttaaggatc   360
caacggtcac cctttctccc aaaccaatct ctaaatgttg tgaagcttag gccaaatttt   420
atgactatat ataggggatt gcaccaaggc agtgacacta ttaagggatc agtgagactc   480
ttttgtataa ctgtagcata tagtactagt aagcagtaat agcaatggcc tcctccatga   540
tctcatcggc aaccattgcc accgtgaact gctcctcccc ggcacaggcc aacatggtgg   600
cccccttcac cggcctcaag tctgcctctg ctttcccagt cactaggaag gccaacaacg   660
acatcacttc tcttgcaagc aatggtggga gagtgcaatg catgcaggta cttggtgatg   720
cataaataca acttaaatta ccccaattgt ttgaacacaa caaattacat aaattgaatc   780
aaatatatat cttggctttt gagtataggt gtggcctcct cttgggaaga agaagttcga   840
gacactctca tacctccccg atcttacacc cgtacagttg gctaaggaag tagattacct   900
tcttcgctct aaatggattc cttgcttgga attcgaatta gaggtgtttt cgagctctaa   960
attattccat tccaacactt tatttttta gtgggatatt tgatttgatt aaatgtgttt    1020
tatatgtatg tgcaggaggg attcgtgcac cgtaagtact cgagcttacc cacgtactac   1080
gatg                                                               1084

<210> SEQ ID NO 6
<211> LENGTH: 36
<212> TYPE: DNA
<213> ORGANISM: Artificial Sequence
<220> FEATURE:
<223> OTHER INFORMATION: Description of Artificial Sequence: primer

```
<400> SEQUENCE: 6
ctgcagcgct catgttaaca attaattcct ataatc                              36

<210> SEQ ID NO 7
<211> LENGTH: 31
<212> TYPE: DNA
<213> ORGANISM: Artificial Sequence
<220> FEATURE:
<223> OTHER INFORMATION: Description of Artificial Sequence: primer

<400> SEQUENCE: 7
gagatcatgg aggaggccat ggctattact g                                   31

<210> SEQ ID NO 8
<211> LENGTH: 550
<212> TYPE: DNA
<213> ORGANISM: Gossypium hirsutum

<400> SEQUENCE: 8
ctgcagcgct catgttaaca attaattcct ataatcgaca tcaaaattat atgaaagaat    60
taacacttgg ttaccgagtt accatatttg aagataaggc gaaaggtaaa aacacaaaag   120
gcaagcatga ccaagcaaac aaggtatgga catagatttt ttttgaatcg ggaatggcca   180
aatgggaccg tgaagagggg acaaaggaga aatcaggcat tcacggtttc cattggatga   240
aatgagataa gatcactgtg cttcttccac gtggcaggtt gccaaaagat aaggctttac   300
cattcaagaa aagtttccac cctctttgtg gtcataatgg ttgtaatgtc atctgattta   360
aggatccaac ggtcacccct tctcccaaac caatctctaa atgttgtgaa gcttaggcca   420
aattttatga ctatatatag gggattgcac caaggcagtg acactattaa gggatcagtg   480
agactctttt gtataactgt agcatatagt actagtaagc agtaatagcc atggcctcct   540
ccatgatctc                                                          550

<210> SEQ ID NO 9
<211> LENGTH: 31
<212> TYPE: DNA
<213> ORGANISM: Artificial Sequence
<220> FEATURE:
<223> OTHER INFORMATION: Description of Artificial Sequence: primer

<400> SEQUENCE: 9
gaaccaggtc gatagttgaa ttagttatgt t                                   31

<210> SEQ ID NO 10
<211> LENGTH: 30
<212> TYPE: DNA
<213> ORGANISM: Artificial Sequence
<220> FEATURE:
<223> OTHER INFORMATION: Description of Artificial Sequence: primer

<400> SEQUENCE: 10
ctcagctgtt tgcatcatgg cagcatcttg                                     30

<210> SEQ ID NO 11
<211> LENGTH: 1370
<212> TYPE: DNA
<213> ORGANISM: Gossypium hirsutum

<400> SEQUENCE: 11
tttcagaacc aggtcgatag ttgaattagt tatgttattg gtccgactag tttgattaaa    60
aattattaaa aattcataaa ataagaatag aaaaatcgct ctaatcaagt tttttagttc   120
```

```
gacaagtacc aattcatgga tcaacctgct taacctcttg ttttggacaa tacctcaacc    180
gcttcttgat ccaatcggtt cggatcacta aataccccct agaaggagat gaggctaagc    240
agagcgaaaa taactttcca cgagacgaga atggaaacta ttgtatttaa atattttgat    300
tggattcaac aatcaatatt ttgtaaaggt aagtatttcc ataaactatt taagaataat    360
gattcttcat gtgcagaacg cggcggtact attttcaaga tacaatacat tactcgacgg    420
aacaattcgt attgcagtac caattatttt aaactgaatg aaatttagaa acacacaaga    480
aaaaaataat ataattataa aagtatcatt gtcttggaac tcagttctat attaattctc    540 attttttggtg tttatatata gaatactaag aggtactgct tctttgaaaa gacacaacat    600
tttccttaga aaaaattatg aatagttata tatatttacg taaagacacc tctctttaat    660
tacatttttc tttctttcct attatatata ttataaataa tataaaactt taatactata    720
tattttattt gaaattactt tataatatat aatataaatt atttatatgt tatatattat    780
atacaacaat tattagtaag ttaagattga atcagaaaaa atattacgag tcaaatagtt    840
ttttactttg ttttataata aaaagtaat taaaataaat ttagccccaa taaaaaaaat    900
taaatctact ctttaggtga aatttttaat taattagtcc ctgaggtaag ctttcggctg    960
ctaagctatg aaattgtcat tatgtataac ttttatgcaa gtgtccctca cctctcggac   1020
acctccctcc ttcacaaaac agcgaggtgt acgctcacgt gtcaatgttg ggttacgtgt   1080
taaggctcca acattccgat ccaccggtca atcccctctg tgtactctgt gtacataagc   1140
tgtgccccat atacaaacac caacggagct caacaaagta tctgtacggt accgcattat   1200
atttttattg acccaccatg ggccagggac aacctaggag gcctcaacaa ccagcaggtc   1260
aaggtgagaa ccaagagcct atcaaatatg gagatgtttt caacgtcagc ggtgagttag   1320
ccaacaagcc tatcgcaccc caagatgcag ccatgatgca aacagctgag                1370
```

<210> SEQ ID NO 12
<211> LENGTH: 30
<212> TYPE: DNA
<213> ORGANISM: Artificial Sequence
<220> FEATURE:
<223> OTHER INFORMATION: Description of Artificial Sequence: primer

<400> SEQUENCE: 12

```
ctgcagtttc agaaccaggt cgatagttga                                        30
```

<210> SEQ ID NO 13
<211> LENGTH: 39
<212> TYPE: DNA
<213> ORGANISM: Artificial Sequence
<220> FEATURE:
<223> OTHER INFORMATION: Description of Artificial Sequence: primer

<400> SEQUENCE: 13

```
ctcctaggtt gtccctggcc catggtgggt caataaaaa                              39
```

<210> SEQ ID NO 14
<211> LENGTH: 1246
<212> TYPE: DNA
<213> ORGANISM: Gossypium hirsutum

<400> SEQUENCE: 14

```
ctgcagtttc agaaccaggt cgatagttga attagttatg ttattggtcc gactagtttg     60
attaaaaatt attaaaaatt cataaaataa gaatagaaaa atcgctctaa tcaagttttt    120
```

```
tagttcgaca agtaccaatt catggatcaa cctgcttaac ctcttgtttt ggacaatacc      180
tcaaccgctt cttgatccaa tcggttcgga tcactaaaat acccctagaa ggagatgagg      240
ctaagcagag cgaaaataac tttccacgag acgagaatgg aaactattgt atttaaatat      300
tttgattgga ttcaacaatc aatatttgt aaaggtaagt atttccataa actatttaag       360
aataatgatt cttcatgtgc agaacgcggc ggtactattt tcaagataca atacattact      420
cgacggaaca attcgtattg cagtaccaat tatttaaac tgaatgaaat ttagaaacac       480
acaagaaaaa aataatataa ttataaaagt atcattgtct tggaactcag ttctatatta      540
attctcattt ttggtgttta tatatagaat actaagaggt actgcttctt tgaaaagaca     600
caacattttc cttagaaaaa attatgaata gttatatata tttacgtaaa gacacctctc     660
tttaattaca tttttctttc tttcctatta tatatattat aaataatata aaactttaat    720
actatatatt ttatttgaaa ttactttata atatataata taaattattt atatgttata    780
tattatatac aacaattatt agtaagttaa gattgaatca gaaaaaatat tacgagtcaa    840
atagtttttt actttgtttt ataataaaaa agtaattaaa ataaatttag ccccaataaa    900
aaaaattaaa tctactcttt aggtgaaatt tttaattaat tagtccctga ggtaagcttt    960
cggctgctaa gctatgaaat tgtcattatg tataacttt atgcaagtgt ccctcacctc    1020
tcggacacct ccctccttca caaacagcg aggtgtacgc tcacgtgtca atgttgggtt     1080
acgtgttaag gctccaacat tccgatccac cggtcaatcc cctctgtgta ctctgtgtac    1140
ataagctgtg ccccatatac aaacaccaac ggagctcaac aaagtatctg tacggtaccg   1200
cattatattt ttattgaccc accatgggcc agggacaacc taggag                    1246
```